United States Patent [19]

Gordon

[11] Patent Number: 5,061,361
[45] Date of Patent: Oct. 29, 1991

[54] CAPILLARY ZONE ELECTROPHORESIS CELL SYSTEM

[75] Inventor: Gary B. Gordon, Saratoga, Calif.

[73] Assignee: Hewlett-Packard Company, Palo Alto, Calif.

[21] Appl. No.: 319,460

[22] Filed: Mar. 6, 1989

[51] Int. Cl.$^5$ .................... G01N 27/26; B01D 57/02
[52] U.S. Cl. ............................ 204/299 R; 204/180.1
[58] Field of Search .............. 204/299 R, 180.1, 183.3; 250/573, 576

[56] References Cited

U.S. PATENT DOCUMENTS

| | | | |
|---|---|---|---|
| 3,623,812 | 11/1971 | Hannig et al. | 356/344 |
| 4,459,198 | 7/1984 | Mizuno et al. | 204/183.3 X |
| 4,816,123 | 3/1989 | Ogan et al. | 204/299 R X |
| 4,898,658 | 2/1990 | Karger et al. | 204/299 R |

*Primary Examiner*—John F. Niebling
*Assistant Examiner*—John S. Starsiak, Jr.

[57] ABSTRACT

A method and apparatus for increasing detector sensitivity in a Capillary Zone Electrophoresis detector is disclosed. The present invention employs a unique cell, fabricated directly into a separations capillary, that increases both the flux and the path length of the ultraviolet light employed in an absorption measurement. The cell employs controlled geometric contours and osmotic pumping to prevent laminar mixing and turbulence. This novel design maintains the resolution of the parent biological separations instrument, while affording an order of magnitude enhancement of in sensitivity. A narrow bore capillary includes an injection end and an output end. Each end is placed in a reservoir containing a buffer solution and a sample of solute. The solute comprises at least one unknown constituent component. An electric field is imposed across the buffer solution and solute in the capillary by a power supply coupled to leads and electrodes. A source of ultraviolet light illuminates a novel cell within the capillary and a sensor measures the absorbance of radiation by the solute to detect the constituent components. A computer may be coupled to absorbance detection circuitry to analyze and display the results of the identification procedure.

20 Claims, 7 Drawing Sheets

CAPILLARY ZONE ELECTROPHORESIS CELL SYSTEM

BACKGROUND OF THE INVENTION

The present invention is an apparatus and method for identifying unknown substances. This invention is particularly concerned with the recognition of large biological materials which are electrophoretically separated in a narrow bore capillary and which are then detected by measuring the amount of ultraviolet radiation absorbed by the unknown substances as they pass through a novel cell that resides within the capillary.

Recent advances in biotechnology have accelerated the demand of research laboratories, health-care facilities, and pharmaceutical manufacturers for devices which are capable of accurately and rapidly identifying extremely small quantities of inorganic and organic substances. Previous techniques, which include gas and liquid chromatography, have been employed to assay samples whose molecular structure is relatively small. Although chromatography may be successfully employed to resolve metals, inorganic mixtures, and small organic ions; the very large and exceedingly complex molecules of amino acids, proteins, peptides, and DNA are more difficult to isolate and discover in a sample of unknown composition. Another serious flaw in chromatographic methods is the predicament that is encountered when the unknown sample is especially sparse, since chromatography utilizes relatively large amounts of the material which requires analysis. Other shortcomings that are experienced when liquid chromatography is practiced include inconsistent patterns of solute movement through the system which creates uneven flows called "dead zones" and undesirable laminar mixing as opposed to bulk movement of the fluids.

Electrophoresis is another well-known procedure that enables the researcher or scientist to evaluate undetermined materials. An electric field is imposed across a length of tubing or capillary that contains a mixture of the unknown sample and a non-reactive liquid often called a buffer solution. The electric field causes the constituents of the unknown sample to migrate through the capillary due to the electrical attraction created by the field. Different components within the sample, however, are attracted at different rates due to their varying molecular drag and varying net electrical charges. Because dissimilar substances do not react to the drag and electrical attraction in the same way, they become increasingly separated into distinct zones or groups as they progress along the capillary. Each band of constituent material that makes up the original unseparated mixture of unknown material passes through the capillary by itself. At some point along this tubing, each band is examined and identified by a detector. One type of detector for electrophoretic separations measures the electrical conductivity of the bands in the capillary. An alternative detection scheme is a method called laser induced fluorescence. Although this technique is highly sensitive, it is costly and is limited to detecting compounds that fluoresce or which can be stimulated to do so. Another previous system probes the unknown material by shining light through the material and then gauging how much light is absorbed by the material. Unfortunately, the short and narrow path that the light travels across the capillary does not provide many opportunities for the undetermined sample to absorb photons. The capillaries must be kept very narrow so that all the material inside it moves easily without turbulence or eddy currents that might be caused by uneven radial heating across a larger tube. As a result of this size constraint, one major problem that plagues this approach is low detection sensitivity.

As the technology of genetic engineering continues to evolve, diagnostic and measurement techniques which are more accurate, reliable, and sensitive become increasingly more valuable. Doctors, clinicians, and laboratory technicians need more powerful tools to explore the intricacies of the genetic code, to improve the hardiness and usefulness of plant and animal life in an effort to feed the world's burgeoning population, and ultimately to devise cures for inherited disabilities and dreaded diseases. The problem of providing a highly sensitive and precise biological detection and analysis system that overcomes the limitations that impair previous devices and techniques has presented a major challenge to designers and innovators in the biochemical arts. The development of an effective, sensitive, affordable, and unerring system for sensing the components of an unspecified biological sample would constitute a major technological advance in the biochemical and biotechnology industries. The enhanced performance that could be achieved using such an innovative device would satisfy a long felt need within the business and would enable manufacturers of drugs, medicines, and biological products to save substantial expenditures of time and money.

SUMMARY OF THE INVENTION

The Capillary Zone Electrophoresis Cell System disclosed and claimed in this patent application provides extraordinarily accurate detection of unknown biological samples at sensitivity levels and cost constraints which are unattainable using conventional analysis methods. The key to the enhanced performance that is achieved using the present invention is a novel cell which is integrally formed within the detection circuit of the narrow bore capillary. The Capillary Zone Electrophoresis Cell System is capable of sensing injected substances at the remarkable sensitivity threshold of one part per million concentration. This revolutionary achievement has been accomplished with an system that is economical, easy to use, and highly reliable.

A tiny capillary with an inside diameter about as thin as a hair conducts a carrier fluid from an injection end to an output end. Both ends of the capillary are placed in reservoirs which also contain the carrier fluid, which is usually called a buffer solution. At the start of the separation, a nano-liter volume of an unknown substance is inserted into the injection end of the capillary. An electric field is then imposed across the capillary. Due to the electrical field, charged component parts of the unknown sample move from one end of the capillary to the other end. During the last stages of their migration, the unspecified constituents of the sample enter a novel egg-shaped cell. While in the cell, ultraviolet light is directed toward and through the cell. Part of the light is absorbed by the biological sample. The level of absorbtion is measured by a detector, and, based upon comprehensive and widely-available knowledge which indicates which types of substances absorb various amounts of light, an analysis of the sample is obtained.

The Applicant's Capillary Zone Electrophoresis Cell System is a diagnostic and measurement device that offers an unprecedented sensitivity in detecting the constituent factors of microscopic samples. The apparatus claimed in this patent application provides an effective, efficient, and powerful tool that will enable engineers and scientists in the medical instrumentation industry to construct analysis equipment that will revolutionize the critically important field of biotechnology.

An appreciation of other aims and objectives of the present invention and a more complete and comprehensive understanding of this invention may be achieved by studying the following description of a preferred embodiment and by referring to the accompanying drawings.

DETAILED DESCRIPTION OF A PREFERRED EMBODIMENT

Figure 1:
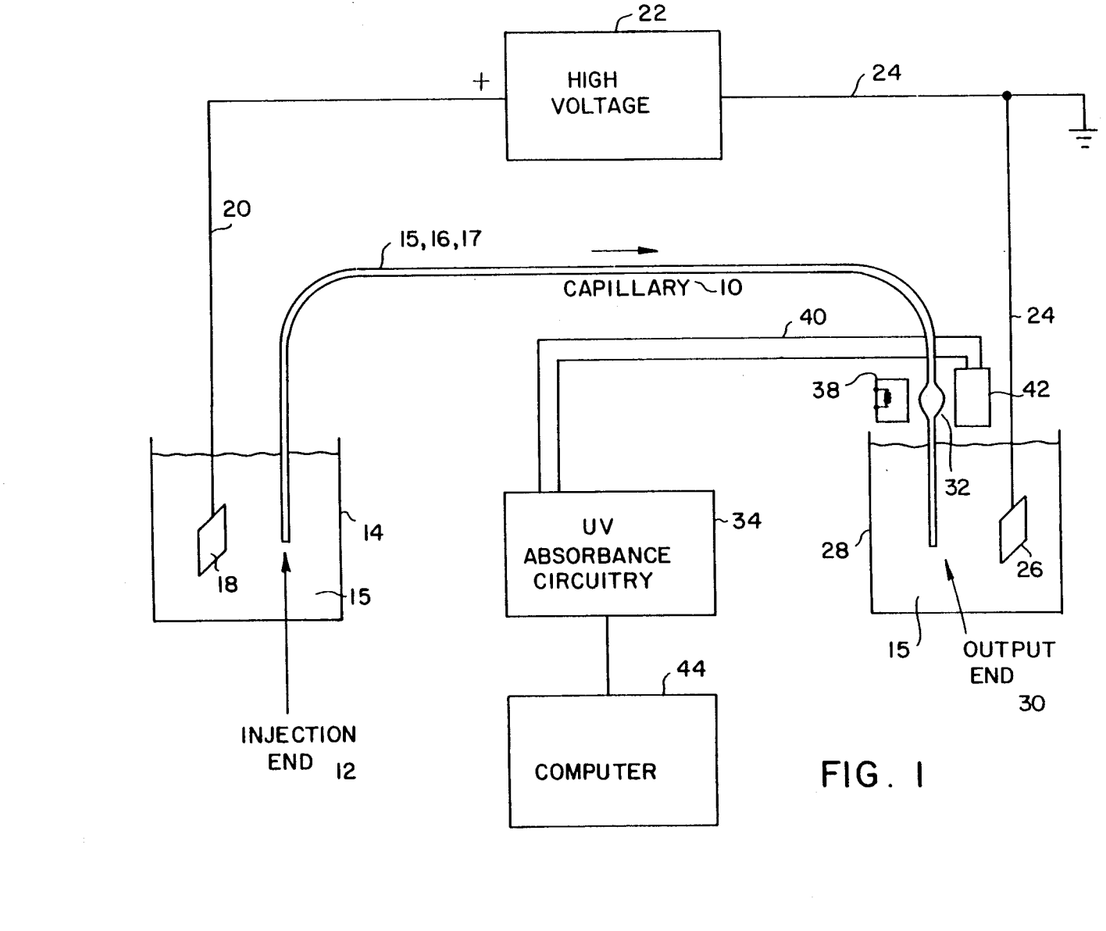
FIG. 1 is a schematic diagram that illustrates a Capillary Zone Electrophoresis Cell System.

FIG. 1 is a schematic illustration of a Capillary Zone Electrophoresis (CZE) Cell System which includes a narrow bore capillary 10 having an injection end 12 located in an injection reservoir 14. The capillary 10 is fabricated from fused silica and measures about 50 microns across its inside diameter, although different-sized micro-bore capillaries are envisioned by the inventor. Injection reservoir 14 supplies the capillary 10 with an electrolytic aqueous medium of constant isocratic solution, such as a simple salt or buffer solution 15. A sample 16 having unknown constituent parts 17 is inserted into the injection end 12 by momentarily dipping the end 12 into a sample vial (not shown) and by drawing a small amount of sample 16 into the capillary 10 by the application of voltage or pressure. A high voltage power supply 22 is connected to a positive electrode 18 which is situated in injection reservoir 14. A ground lead 24 connects the power supply 22 to a negative electrode 26, which is similarly located in an output reservoir 28. An output end 30 of capillary 10 is placed in output reservoir 28.

A novel cell 32 is formed within the capillary 10 and is illuminated by a source of ultraviolet (UV) light 38. Throughout the specification and claims, the terms "containment means", "dilated zone", and "cellular containment means" refer to the cell as pictured in the drawings and as described by the specification. A detector 42 receives light from source 38 after it passes through the cell 32 and is absorbed by components 17 of any solutes 16 that are carried in the buffer solution 15. The detector 42 is connected to ultraviolet absorbance circuitry 34 by leads 40. Measurements may be interpreted and displayed by a computer 44 or by a strip-chart recorder (not shown) which receives signals from the absorbance circuitry 34.

Figure 2:
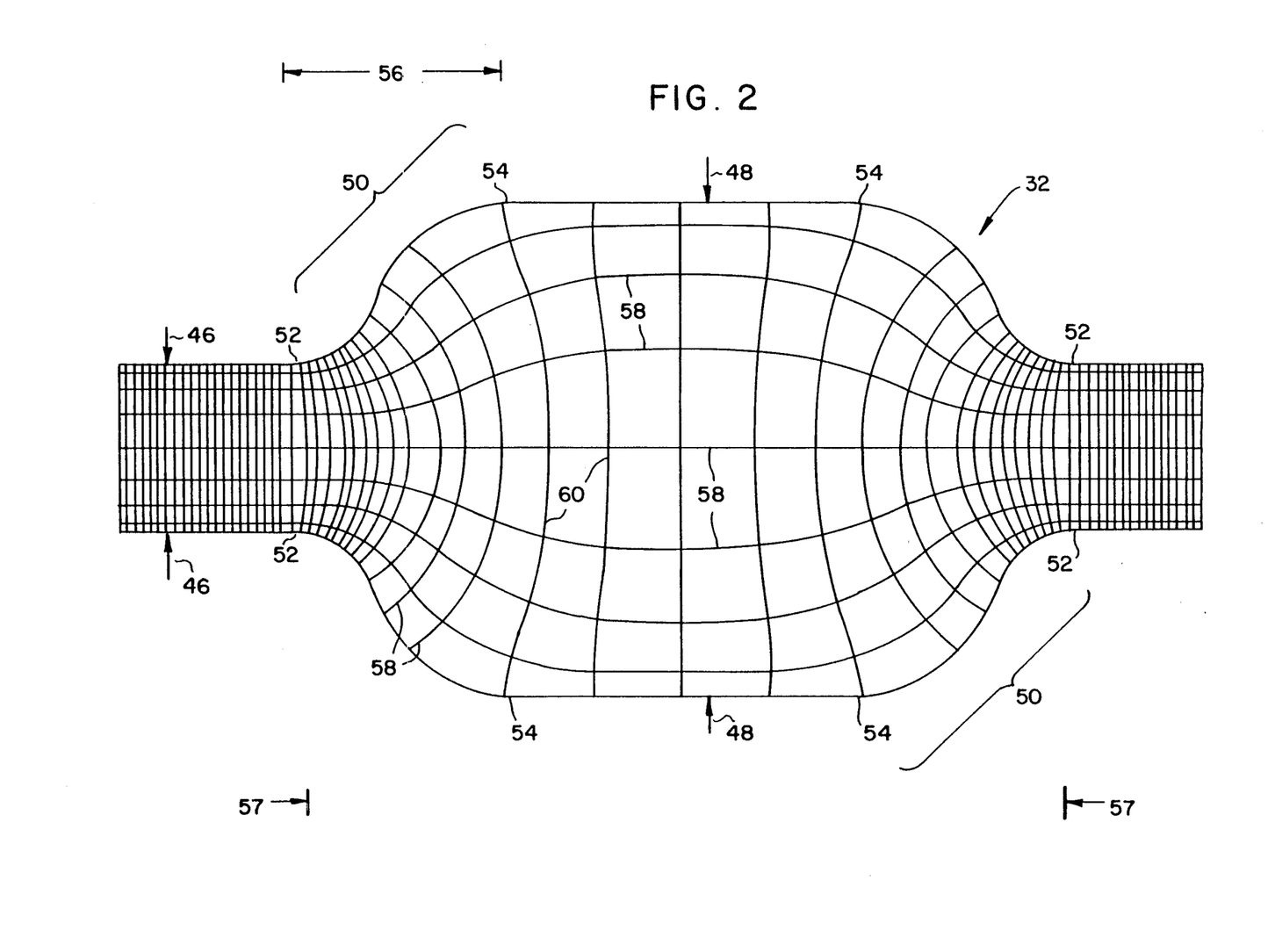
FIG. 2 is a side view of the cell showing the electric field and isopotential lines.

FIG. 2 reveals one embodiment of the novel cell 32 in great detail. The smallest diameter of the cell 32 is represented by the distance across the pairs of arrows labeled "46". In the best mode of the invention, this dimension is fifty microns and matches the inside diameter of the narrow bore capillary 10 and is a part of the capillary 10. The greatest diameter of cell 32 is slightly larger than capillary 10 and is indicated by the pair of arrows labeled "48". In this embodiment, the maximum diameter 48 of the cell 32 is one hundred and fifty microns. A curved portion of the cell 32 is delineated by reference numeral 50. The end points of the curved portion 50 of the cell 32 are marked by reference numerals 52 and 54. A distance 56 shown in the upper left portion of FIG. 2 represents the longitudinal projection of the curved portion 50 of cell 32. In one embodiment of the present invention, the longitudinal projection 56 is within an order of magnitude of the greatest diameter 48 of the cell 32. The total length of the cell 32 is marked by reference numerals 57, which appear at the bottom of FIG. 2. In another embodiment of the present invention, the total length 57 is approximately equal to the greatest diameter 48. Horizontal lines 58 illustrate electric field lines generated by the influence of power supply 22 and electrodes 18 and 26. Vertical lines 60 reveal lines of equal potential. In this illustration, the volume of the cell 32 is equivalent to the volume of 1.6 mm of capillary length. This volume is measured in nanoliters. This remarkably tiny volume utilized by the Capillary Zone Electrophoresis Cell constitutes an improvement of a full three orders of magnitude of miniaturization over cells fabricated for liquid chromatography detection.

Figure 3:
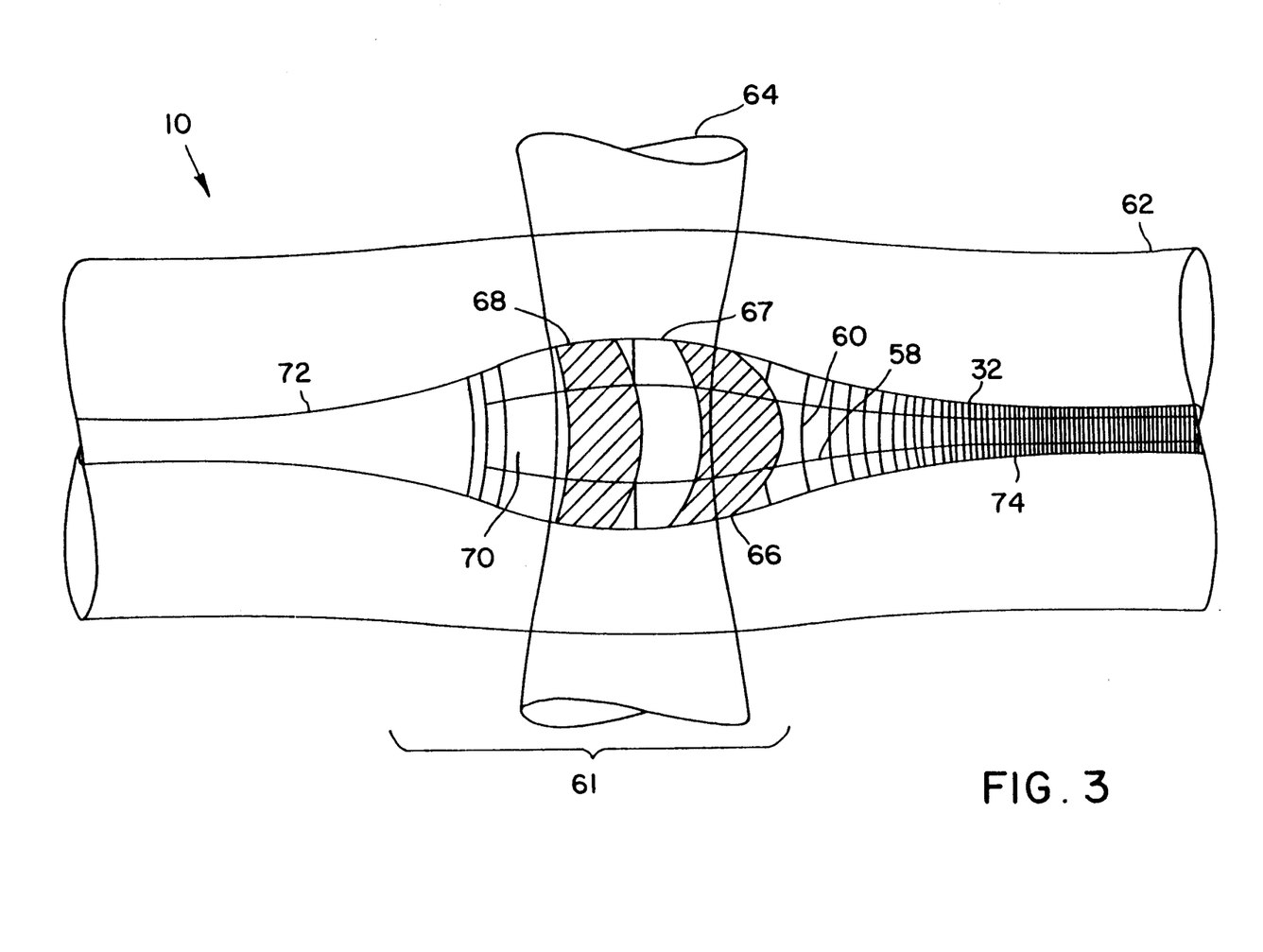
FIG. 3 is a side view of the cell that also reveals bands of solute borne by the buffer solution passing through a beam of ultraviolet radiation.

FIG. 3 depicts yet another embodiment of the CZE cell 32 which has an elongated central portion 61 that extends in either direction to a narrow portion 74. The outside diameter of capillary 10 is indicated by the reference numeral "62". A beam of ultraviolet radiation 64 is directed toward the center of the cell 32 so that the axis of the radiation 64 is perpendicular to the longitudinal axis of the capillary 10. The wavelength of the radiation employed is usually in the range of 200 to 400 nanometers (nm). The band at the right side of the center of cell 32 represents a first distinct group of solutes or analytes 16 migrating from left to right, typically comprising a tenth of a unit of volume called a "peak". These bands of solute, labeled 66 and 68, are often referred to as "fractions of peaks" because they collectively correspond to a graphic peak or spikes of an electropherogram which displays increased levels of UV light absorbtion along an abscissa scaled in detector voltage, and across an ordinate marked in units of time. As each constituent part 17 of an unknown sample 16 passes through the cell 32, the light absorbed by the constituent parts 17 increases, and reduces the amount of radiation that falls on the sensor 42. The resulting graph is a series of Gaussian distributions which identify the materials in the capillary 10. In this illustration, each band 66 and 68 shown in FIG. 3 represents one-tenth of a width of a typical narrow peak.

Figure 4A:
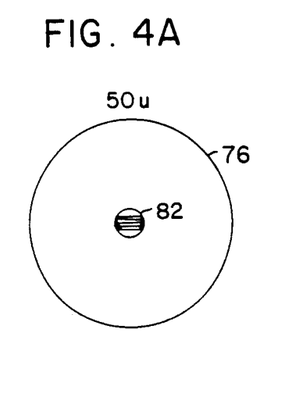
FIG. 4 is a schematic comparison of photon flux and path length through three different size capillary cross-sections.
Figure 4B:
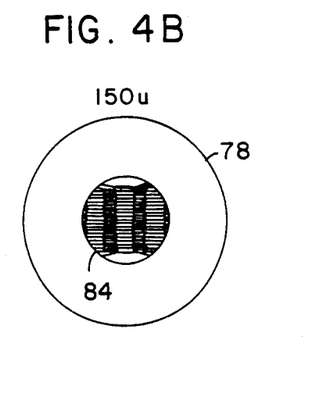
Figure 4C:
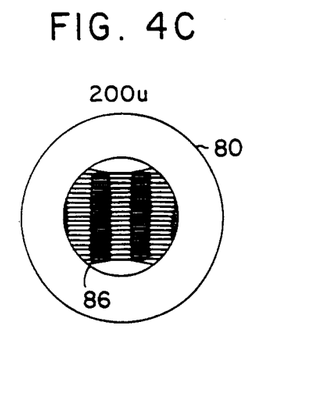

FIGS. 4(a), (b), and (c) exhibit the cross-sections of three combinations of outer capillaries and enclosed cells having increasingly larger diameters available for conduction of the buffer solution 15 and the solute 16. Capillary outside diameters 76, 78, and 80 correspond to a 50 micron cell 82, a 150 micron cell 84, and a 200 micron cell 86, respectively. The cross hatching shown within each cell 82, 84, and 86 represents the flux density of photons striking the cells which are available for absorption. The increased optical path length provided by the larger bores contributes directly to an increase in sensitivity and a concomitant decrease in noise levels. The sensitivity increases by the multiple of enhanced photon path length and by the square root of the path's cross-sectional area, due to the larger flux of radiation. If cell 82 in FIG. 4(a) is taken as a reference, cell 84 provides an increase in sensitivity of $3\sqrt{3}$ or nearly five times an improvement in sensitivity. The 200 micron cell 86 develops a sensitivity capability over eight times that of the reference cell 82, based on the product of the increased path length, 4, and the larger radiation density $\sqrt{4}$. The improvement is actually even greater than this value, since the present invention avoids the problem of stray light—flux that spills around the sides of the cell—which disproportionately penalizes smaller previous cells.

Figure 5:
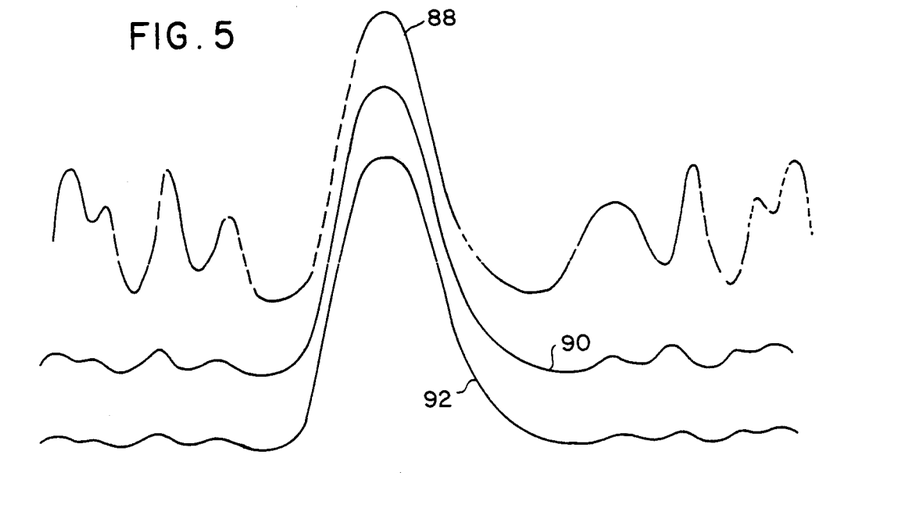
FIG. 5 is a comparison of normalized detected bands showing the reduction in noise achieved by the using successively larger cell diameter sizes shown in cross-section in FIG. 4.

The three curves 88, 90, and 92 depicted in FIG. 5 correspond to the results of employing cells 82, 84, and 86 shown in FIG. 4. The three curves are normalized to show the progressive reduction in signal noise. Curve 92, a consequence of using the 200 micron cell 86, reflects a substantially depressed noise level compared to curve 88, which reports the results of using the reference cell 82 which is only 50 microns across. One penalty incurred by increasing the size of the cell is the broadening of the peaks. FIG. 5 shows that the width of peak 92 is slightly larger than that of peak 88. The degree of broadening experienced in this example is approximately ten percent. Since the resolution of the CZE detector is measured by the separation between peaks, broader peaks degrade the performance of the system. The ten percent degradation seen here, however, is relatively insignificant compared to the ten-fold gains in sensitivity achieved by employing the novel CZE cell which provides for increased optical path length and flux.

Figure 6:
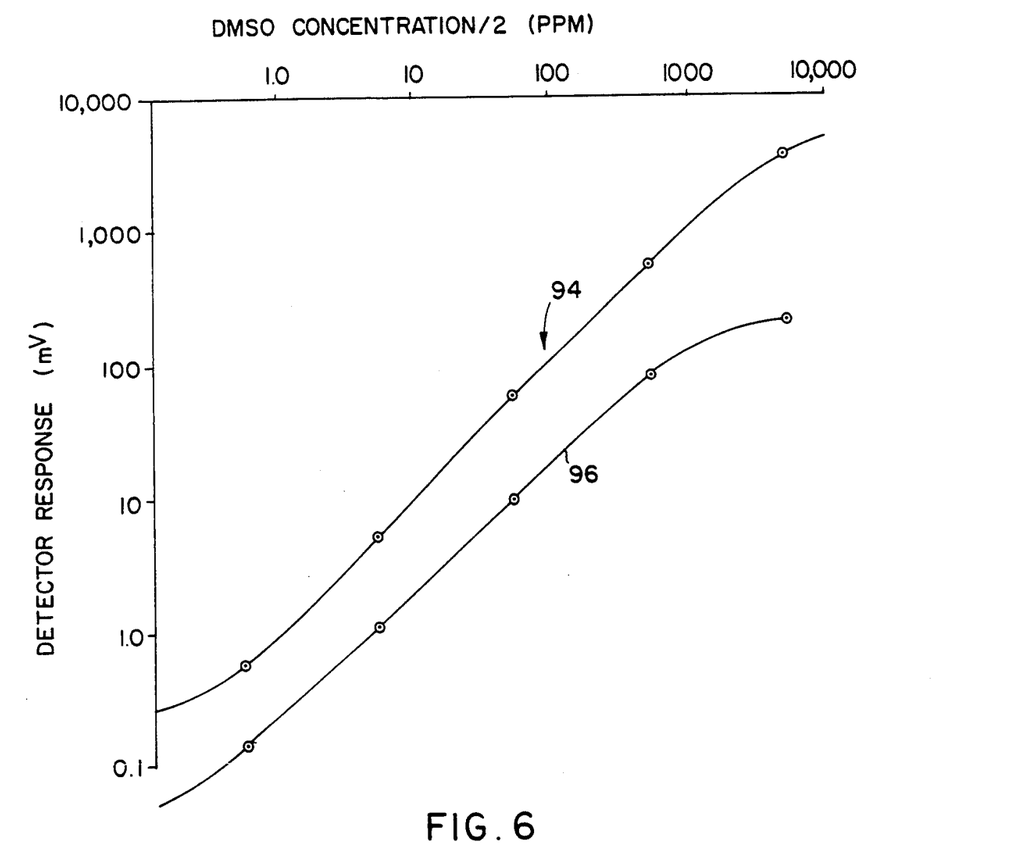
FIG. 6 is a graph which plots detector response against the concentration of a detected solute and which illustrates the desirable linear characteristic of the present invention.

FIG. 6 exhibits the strong and desirable linear characteristic of the present invention. Curves 94 and 96 are graphs of detector response in millivolts (mV) for a sample absorber, DMSO. Curve 94 was generated using a log amplifier in the measurement equipment. The use of a log amplifier introduces noise to the system, but the resulting plot shows greater linearity at strong concentrations. Curve 96 was generated using a linear amplifier. This mode of measurement offers lower noise and higher sensitivity. A log operation can be performed after the signals are amplified above the circuit noise level to combine the sensitivity of curve 96 with the linearity of curve 94. The extended linearity of both curves 94 and 96 is far greater than that attainable with previous methods that utilize detection on conventional capillaries without the novel cell 32 claimed in this application, because the novel cell 32 helps to eliminate stray light that would otherwise skirt the sides of a much smaller target and that would not pass through the solute 16.

Figure 7:
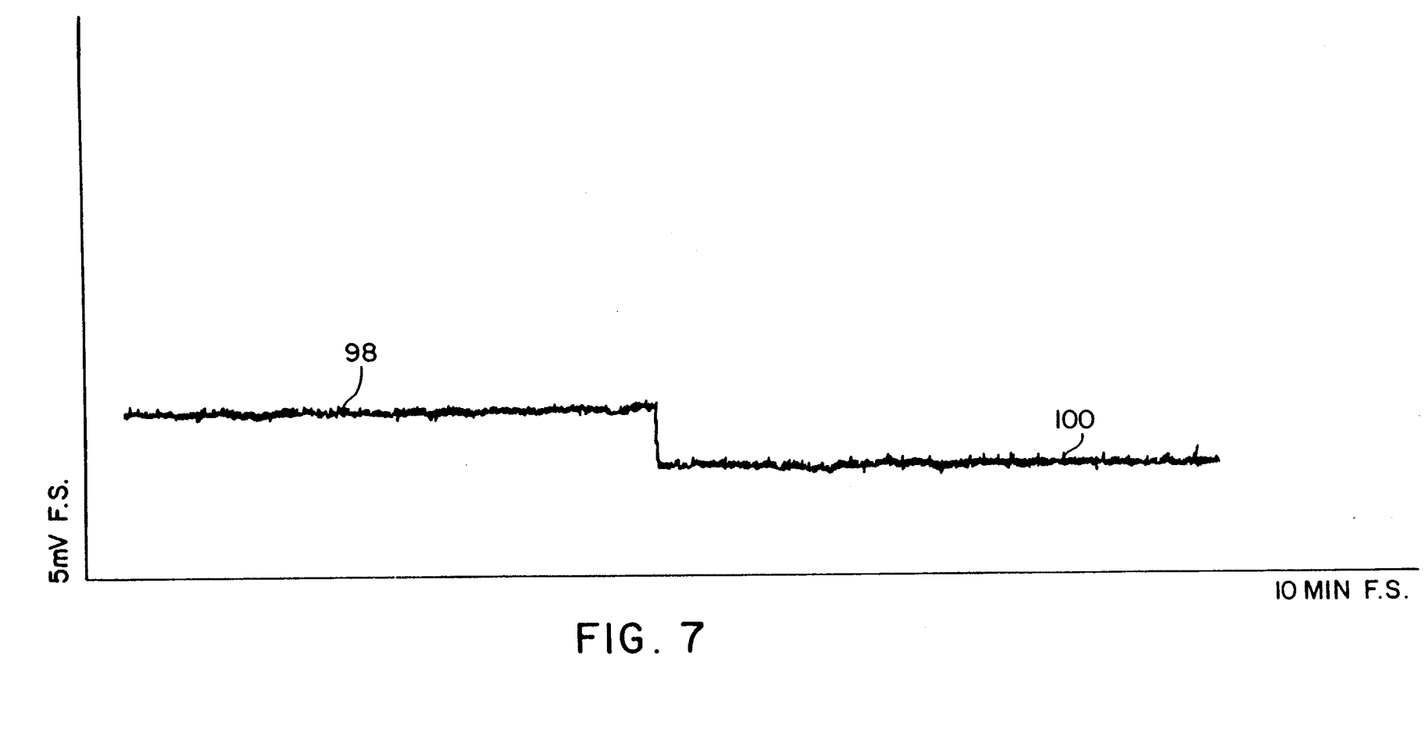
FIG. 7 is a graph which dramatically reveals the remarkable sensitivity of the Capillary Zone Electrophoresis Cell System. The sharp drop in the curve from left to right shows the abrupt change in absorbance of a protein equivalent present in the cell at a concentration level of only one part per million.

FIG. 7 reveals the striking results of placing less than one part of average protein equivalent in a million parts of buffer solution and passing the mixture through the detector. The left portion of the curve 98 is a detector output showing a first level of absorbance of pure buffer solution. When the one part per million of protein equivalent passes into the CZE cell, the absorbance increases dramatically, as indicated by the reduced detector output shown by the right portion of the curve, labeled 100. This one drawing vividly expresses the power of the present invention to sense complex biological substances in minute concentrations.

Figure 8:
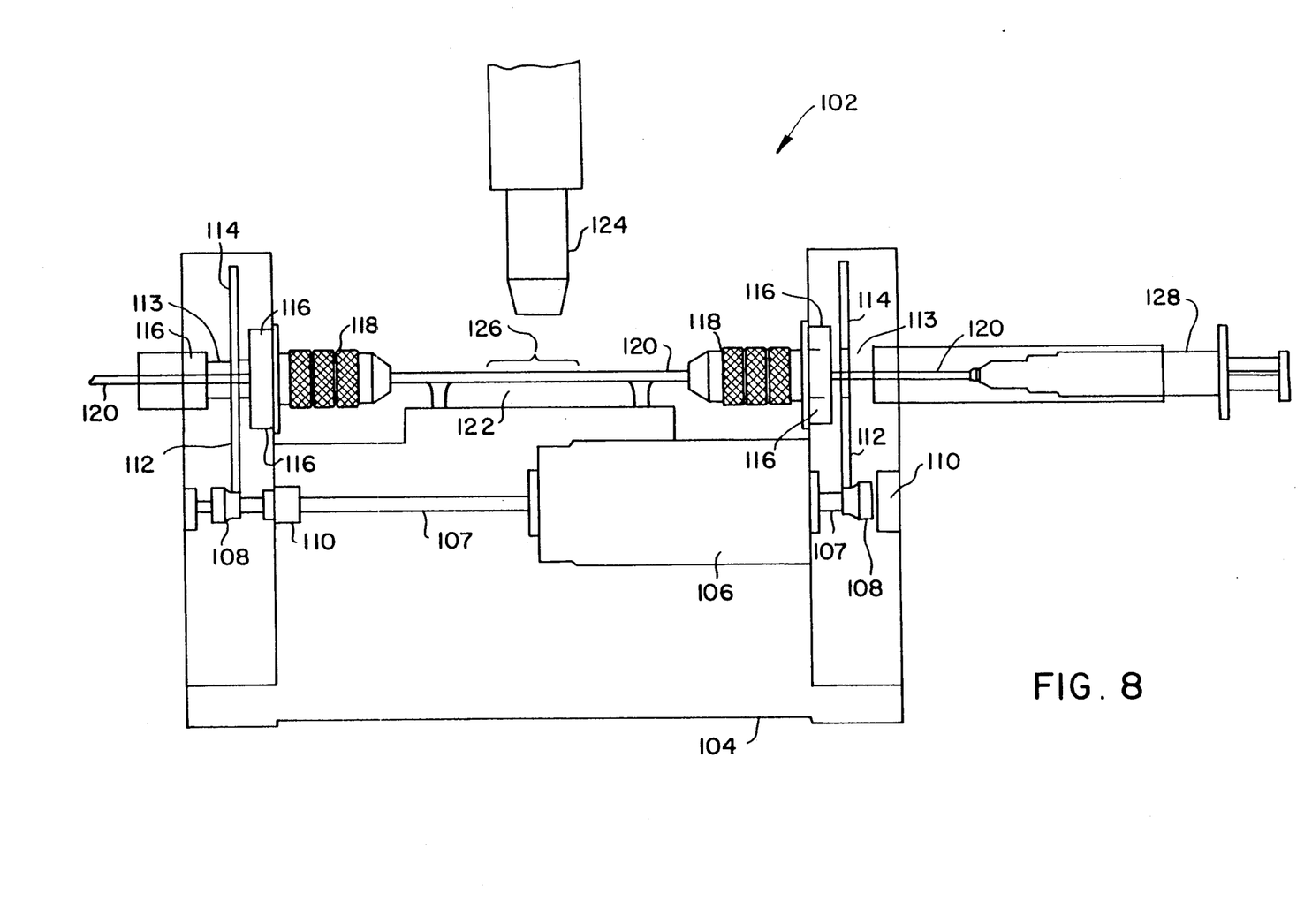
FIG. 8 is a schematic side view of a glass lathe that is employed to fabricate the novel CZE cell.

FIG. 8 is a schematic side view of a cell lathe 102 that is employed to fabricate the novel CZE cell 32. The lathe 102 includes a base 104 that anchors motor 106 which is connected by a drive shaft 107, supported by bearing 110, to drive gears 108. Drive gears 108, in turn, are coupled to driven gears 112 and 114, which are mounted on rotating hollow shafts 113 supported by bearings 116. Chucks 118 are mounted on hollow shafts 113 and provide support for capillary 120 at two points. Capillary 120 is bolstered by support 122 and is held by a pair of chucks 118. The operator of the lathe 102 views a central section of capillary 126 that is heated by a small flame through microscope 124. Micro-blowing methods that scaled-down versions of techniques which are well-known to persons ordinarily skilled in the glass fabrication art were employed to manufacture the CZE cells 32. The capillary 120 is first sealed off at one end, and then a syringe 128 is used at the other end to pressurize the volume within it to ten to twenty percent over-pressure. A high quality cell 32 may be formed by rotating the capillary 10 in a 1/16" gas flame for three or four seconds.

Operation of the CZE System

The motivating force which drives the separation of analytes in the present invention is an electric field which is imposed across the capillary. A potential difference of thirty to fifty kilovolts causes substances borne by the carrier to move from one end of the tube to another, but the movement itself has two components. The more apparent and more readily understood of the two is electrophoretic migration. Electrophoresis refers to the process of charged molecules moving toward an oppositely charged electrode due to the simple electrical attraction of dissimilar charges. The second reason for movement of materials through the CZE system is a phenomenon called electro-osmotic flow. Whenever a liquid is placed in a glass tube, molecules in the liquid that have a negative charge tend to stick to the walls of the tube. Positive charges do not behave this way. This preferential sticking or absorbtion of negatively charged molecules attracts a thin layer of positively charged molecules all along the inner walls of the capillary. The electric field pulls these positive molecules or ions toward the negative electrode at the output end of the capillary. The positive ions drag other molecules along with them, even those having a neutral or negative charge. The result is a flow of all kinds of differently charged solute moving toward the output end of the capillary. Electro-osmotic flow provides the pumping force which moves molecules of all charges toward one end of the system.

The strength of the electro-osmotic force that generates the bulk flow in the capillary is directly proportional to the applied electric field. Within the CZE cell, the field is lower than the strength of the field in the capillary due to the larger cross-section of conductive fluid within the cell. Since the field is inversely proportional to the fluid area, the field is only one sixteenth as strong within a cell that has a diameter that is four times greater than that of the capillary. In this cell, the osmotic force at the capillary wall within the cell is also sixteen times weaker than the osmotic force at the walls in the rest of the capillary. If the flow velocity were constant, this force would be too small and would result in a laminar flow in which solute at the edge of the cell would lag behind solute in the center of the cell. This uneven transport would cause undesirable spreading of the peaks and would degrade the performance of the CZE system. As a direct consequence of the design of the present invention, this problem does not occur. As this osmotic bulk-flow force drops in the cell, the flow velocity in the cell also drops in proportion to the cross-sectional area of the cell. When the bulk flow slows down in the cell, the forces that propel it fall concomitantly. The extremely beneficial result is a balance of forces on the bands of analyte and an absence of forces that would tend to distort the bands and broaden the peaks.

Design Considerations

Turbulence

One of the primary concerns taken into account when the cell 32 is designed and fabricated is reduction of turbulence. An important feature of the invention is the gradual curvature of the cell. Sharp edges, fittings, gaskets, or joints in the capillary circuit, which are common in liquid chromatography systems, would also denigrate the performance of the detector and are avoided by providing gently sloping curves and transitions. The smooth flow that results from the careful observance of these design constraints avoids turbulence.

Capillary size

The two characteristics that contribute to the quality of a separation of materials in the capillary are selectivity, the ability to definitively separate similar solutes, and sensitivity, the degree to which small amounts of solute can be detected. A CZE system can be made more sensitive by increasing the diameter of the capillary. Larger bore capillaries are more sensitive because their greater diameter supplies a longer path length for light to pass through them. As a consequence, more opportunities are provided for the solute to absorb ultraviolet radiation. The same systems can be made more selective by reducing the diameter of the capillary. Small bore capillaries below 50 microns in diameter do not experience the undesirable radial temperature gradients that are created by the excessive heat which is generated in larger systems. These radial temperature gradients cause the analyte in the center of the capillary to migrate faster than the analyte at the edge, which broadens the peaks and degrades resolution. The unwanted thermal gradients adversely affect molecules of solute as they are being separated by reducing the sharpness of the boundaries of the bands of solute that form in the capillary. When the definition of these bands is compromised, the solute "peaks" become broadened, and the selectivity of the separation is degraded. The novel method and apparatus claimed and disclosed in this patent application resolve the conflicting design considerations concerning selectivity and sensitivity by providing superior performance without having to trade one measure of quality for another.

Advantages over Liquid Chromatography-Type Cells

The present invention offers several significant improvements over conventional liquid chromatographic cell fabrication techniques. Liquid chromatography (LC) is limited by a cell size that is one thousand times greater than CZE and by a cell geometry that produces cells with sharp corners known as "unswept volumes". These pockets cause solutes to hang in the cell, to broaden the detected peaks, and to degrade selectivity. Another disadvantage of LC cells is that the flow through them is laminar—the buffer at the center of the cell moves the fastest, while the buffer at the edge sticks to the edge of the cell. In theory, the flow develops a parabolic velocity profile across the tube in which it flows. This nonlinear profile impairs the performance of the cell because the shape of each band of solute is distorted by this uneven flow. The LC cell must, therefore, be nearly an order of magnitude smaller than the smallest LC peak volumes, so that the peaks are not broadened and selectivity is not sacrificed.

The Capillary Zone Electrophoresis Cell System provides an accurate, powerful, and reliable tool for diagnosis and measurement across a broad spectrum of medical and manufacturing applications. This invention constitutes a major step forward in the continually evolving fields of biotechnology and chemistry.

Although the present invention has been described in detail with reference to a particular preferred embodiment, persons possessing ordinary skill in the art to which this invention pertains will appreciate that various modifications and enhancements may be made without departing from the spirit and scope of the claims that follow.

What is claimed is:

1. An apparatus for detecting at least one component in a sample comprising:

a containment means for conveying a carrier and said sample; said containment means including a section having an inlet with a predetermined cross-sectional area and an outlet;

a kinetic means for moving said sample through said containment means;

a cell coupled between said inlet and outlet of the section of the containment means for holding a small portion of said carrier and said sample; said cell having a greatest cross-sectional area which is normal to a longitudinal flow direction of the cell and which is larger than said predetermined cross-sectional area; and detection means for sensing said component.

2. An identification system comprising:

a tubular vessel capable of receiving a transport medium and a substance having at least one constituent component;

an electric field generator which imposes an electric field across said tubular vessel;

a dilated zone located between an injection end and an output end of said tubular vessel; and a radiation source and a radiation sensor that together measure the effect on radiation passed through said dilated zone.

3. A Capillary Zone Electrophoresis Cell System comprising:

a narrow bore capillary having an injection end and an output end; said capillary including a section with an inlet having a predetermined cross-sectional area and an outlet; said inlet and outlet being respectively coupled to said injection and output ends of the capillary; said capillary being filled with a buffer solution and an analyte; said analyte including at least one constituent component;

an injection reservoir disposed to receive said injection end of said capillary and an output reservoir disposed to receive said output end of said capillary; both of said injection and said output reservoirs being disposed for holding said buffer solution and said analyte;

a power supply coupled to said injection and output ends of said capillary for producing an electric field for moving said buffer solution and said analyte through the capillary;

a cell coupled between the inlet and outlet of the section of said capillary; said cell having a longitudinal flow direction and a greatest cross-sectional area which is normal to the longitudinal flow direction and which is larger than said predetermined cross-sectional area; and an ultraviolet absorbance detector that includes an ultraviolet light source and a sensor; said source and said sensor being coupled to the cell so that said detector is operable for sensing said one constituent component in the analyte.

4. A Capillary Zone Electrophoresis Cell System as claimed in claim 3 in which said cell is characterized by a length which spans a distance between said inlet and outlet of the section of said capillary; said cell further including a greatest diameter that is measured perpendicular to said longitudinal flow direction; and said length being approximately equal to the greatest diameter of said cell.

5. A Capillary Zone Electrophoresis Cell System as claimed in claim 3 in which said cell is characterized by a greatest diameter and includes a curved portion having a longitudinal projection along said longitudinal flow direction; and said longitudinal projection having a length that is within an order of magnitude of said greatest diameter of said cell.

6. A method of identifying an unknown sample comprisiing the steps of:
providing a tubular vessel which includes a section for holding a transport medium and a substance having a least one constituent component; said section having an inlet with a predetermined cross-sectional area and an outlet;
imposing an electric field across said tubular vessel to move said substance through said vessel;
directing a beam of radiation toward said substance while it passes through a cell which is coupled between the inlet and outlet of said section; said cell having a greatest cross-sectional area which is normal to a longitudinal flow direction of said cell and which is larger than said predetermined cross-sectional area; and
measuring a level of radiation absorbed by said substance to identify said constituent component.

7. An apparatus for detecting analytes eluting from a separation process column:
an ultra-violet transparent capillary tube means for carrying analytes borne in a carrier solution;
a cellular containment means for analyzing said analyte; said cellular containment means being integrally formed with said capillary tube means and having a diameter slightly larger than said capillary tube means;
an electrophoretic means for moving said analytes through said capillary tube means;
an ultra-violet light source means for illuminating a central portion of said cellular containment means;
a light sensing means for monitoring a varying light intensity leaving said cellular containment means; and
an amplification means for responding to said light sensing means and for displaying an electronic output that indicates a concentration of analyte in said cellular containment means.

8. An apparatus as claimed in claim 7, in which said light sensing means is a photodiode.

9. An apparatus as claimed in claim 7, in which said light sensing means is a photomultiplier tube.

10. An apparatus as claimed in claim 7, in which said light sensing means senses an absorbtion of ultra-violet light by said analyte.

11. An apparatus as claimed in claim 7, in which said light sensing means senses a fluorescence light emitted by said analyte.

12. An apparatus as claimed in claim 7, in which said cellular containment means is fabricated by
heating a small portion of said capillary tube means; and
pressurizing said capillary tube means to dilate said capillary tube means to form said cellular containment means.

13. The apparatus as recited in claim 1 wherein said cell is an integral portion of said containment means.

14. The apparatus as recited in claim 1 wherein said cell includes a length which spans a distance between the inlet and outlet of said section of the containment means; said cell further including a greatest diameter that is measured perpendicular to the longitudinal flow direction of the cell; and said length being at least equal to said greatest diameter.

15. The apparatus as recited in claim 14 wherein the length of said cell is in the range between two and five times the greatest diameter of said cell.

16. The apparatus as recited in claim 1 wherein said section of the containment means is made from a prescribed material and said cell is made from a material substantially the same as said prescribed material.

17. The apparatus as recited in claim 1 wherein said cell includes a greatest diameter measured perpendicular to the longitudinal flow direction of said cell; said cell further including a curved portion having a longitudinal projection along said longitudinal flow direction; and said longitudinal projection being a length that is within an order of magnitude of the greatest diameter of said cell.

18. The apparatus as recited in claim 1 wherein said sample is moved with a flow velocity in the longitudinal flow direction in the cell via electro-osmotic forces; wherein the cell further includes a curved portion comprising a succession of cross-sectional areas which are normal to the longitudinal flow direction and which change in area from said predetermined cross-sectional area to said greatest cross-sectional area; wherein said curved portion being so constructed and arranged that said electro-osmotic flow force changes in proportion to the respective cross-sectional areas of the curved portion so that said flow velocity remains substantially constant.

19. The invention as recited in claim 3 wherein said analyte is moved with a flow velocity in the longitudinal flow direction in the cell via electro-osmotic forces; wherein the cell further includes a curved portion comprising a succession of cross-sectional areas which are normal to the longitudinal flow direction and which change in area from said predetermined cross-sectional area to said greatest cross-sectional area; wherein said curved portion being so constructed and arranged that said electro-osmotic flow force changes in proportion to the respective cross-sectional areas of the curved portion so that said flow velocity remains substantially constant.

20. The method of claim 6 wherein said cell is an integral portion of the section of said tubular vessel.

* * * * *